United States Patent [19]
Wise et al.

[11] Patent Number: 6,071,982
[45] Date of Patent: Jun. 6, 2000

[54] BIOERODIBLE POLYMERIC SEMI-INTERPENETRATING NETWORK ALLOYS FOR SURGICAL PLATES AND BONE CEMENTS, AND METHOD FOR MAKING SAME

[75] Inventors: Donald L. Wise, Belmont; Joseph D. Gresser, Brookline; Debra J. Trantolo, Princeton; Yung-Yueh Hsu, Norwood, all of Mass.

[73] Assignee: Cambridge Scientific, Inc., Belmont, Mass.

[21] Appl. No.: 08/844,378

[22] Filed: Apr. 18, 1997

[51] Int. Cl.⁷ .................................. A61F 2/00; C08K 3/24
[52] U.S. Cl. .......................... 523/113; 523/114; 523/115; 524/414; 525/411; 525/415; 525/439; 525/445; 525/903; 623/16; 424/426
[58] Field of Search ...................................... 523/113, 114; 524/414; 525/903, 411, 415, 439, 445; 623/16; 424/426

[56] References Cited

U.S. PATENT DOCUMENTS

| | | | |
|---|---|---|---|
| 3,887,699 | 6/1975 | Yolles | 424/19 |
| 4,450,150 | 5/1984 | Sidman | 424/1.1 |
| 4,568,559 | 2/1986 | Nuwayser et al. | 427/3 |
| 4,591,496 | 5/1986 | Cohen et al. | 424/15 |
| 4,623,588 | 11/1986 | Nuwayser et al. | 428/402.24 |
| 4,637,931 | 1/1987 | Schmitz | 424/78 |
| 4,722,948 | 2/1988 | Sanderson | 523/115 |
| 4,767,628 | 8/1988 | Hutchinson | 424/426 |
| 4,780,319 | 10/1988 | Zentner et al. | 424/476 |
| 4,818,542 | 4/1989 | DeLuca et al. | 424/491 |
| 4,843,112 | 6/1989 | Gerhart et al. | 523/114 |
| 4,975,280 | 12/1990 | Schacht et al. | 424/428 |
| 5,134,122 | 7/1992 | Orsolini | 514/15 |
| 5,248,700 | 9/1993 | Lance | 514/772.3 |
| 5,286,763 | 2/1994 | Gerhart et al. | 523/115 |
| 5,336,505 | 8/1994 | Ng et al. | 424/486 |
| 5,385,887 | 1/1995 | Yim et al. | 514/21 |
| 5,397,572 | 3/1995 | Coombes et al. | 424/426 |
| 5,439,688 | 8/1995 | Orsolini et al. | 424/489 |
| 5,456,917 | 10/1995 | Wise et al. | 424/426 |
| 5,502,092 | 3/1996 | Barrows et al. | 521/64 |
| 5,645,592 | 7/1997 | Nicolais et al. | 623/16 |

FOREIGN PATENT DOCUMENTS 60-181029  9/1985  Japan .

OTHER PUBLICATIONS

Gresser, "Preliminary Testing of an Implantable System for Sustained Delivery of Disulfiram for the Treatment of Alcoholism", *Biopolymeric Controlled Release Systems*, vol. II:67–75, 1989.

Kitchell et al., "Preparation of Biodegradable Levonorgestrel Rods", *Long-Acting Contraceptive Delivery System* pp. 164–168, 1984.

Marcotte et al., "Delayed Release of Water-Soluble Macromolecules From Polylactide Pellets", *J. of Controlled Release*, 9:75–85, 1989.

Phillips et al., "Sustained-Release Characteristics of a New Implantable Formulation of Disulfiram", *J. of Pharmaceutical Sciences*, 73:1718–1720, 1984.

*Primary Examiner*—Andrew E. C. Merriam
*Attorney, Agent, or Firm*—Weingarten, Schurgin, Gagnebin & Hayes LLP

[57] ABSTRACT

A bioerodible polymeric semi-IPN alloy which comprises a first bioerodible polymer capable of producing acidic products upon hydrolytic degradation; a second bioerodible polymer, which provides a biopolymeric scaffolding or internal reinforcement; and optionally a buffering compound that buffers the acidic products within a desired pH range. In a preferred embodiment, the second bioerodible polymer comprises polypropylene fumarate (PPF), which is crosslinked, desirably by a vinyl monomer such as vinyl pyrrolidone (VP) to form the biopolymeric scaffolding which provides the semi-IPN with dimensional and geometric stability.

30 Claims, 2 Drawing Sheets

BIOERODIBLE POLYMERIC SEMI-INTERPENETRATING NETWORK ALLOYS FOR SURGICAL PLATES AND BONE CEMENTS, AND METHOD FOR MAKING SAME

FIELD OF THE INVENTION

The invention relates to implantible biomaterials, in particular to bioerodible polymers and more specifically to bioerodible polymers suitable for use in forming internal fixation devices (IFDs) such as bone supports, plates, and pins, and/or bone cements for bone repair.

BACKGROUND OF THE INVENTION

A study in the mid-1980's estimated that about four and a half million people suffer fractures each year in the United States alone. In adults, fractures of the radius and/or ulna of the forearm, and fibula or ankle bone are frequently treated by immobilizing the fracture by the surgical attachment of a metal plate adjacent the fracture. Similarly, in some adults and most children, fractures of the neck of the femur or hip are frequently treated by immobilizing the fracture with a metal plate. In addition to its use in treating fractures of the radius, ulna and femur, a metal plate may also used to immobilize other bones in both the treatment of fractures and in corrective surgery. The metal plate, typically made of a titanium-based metal, a stainless-steel, or a cobalt-chromium metal, is attached to the bone by bone screws. It should be noted that although the immobilization device is referred to as a plate, its size and shape is dictated by the application in which it is to be used.

As the bone heals it is necessary to remove the metal plate by means of a second surgical intervention. The reason for this is that the presence of the metal plate adjacent the bone ultimately results in what is referred to as "plate induced osteopenia" or loss of bone mass. The reasons for this loss of bone mass are not fully understood but appear to be related both to changes in bone stress and changes in bone blood flow. Such bone remodeling in children may lead to growth restriction, especially when plates are used in craniofacial or maxillofacial intervention to repair congenital deformities.

Thus it is desirable to replace metallic surgical plates presently used in surgical procedures with a bioerodible polymer, i.e., one that will dissolve and be absorbed by the body as the underlying bone heals. With such a bioerodible plate, the necessity of a second surgical operation and its concomitant trauma is removed and the deleterious effects caused by the presence of a plate for a long period of time. Furthermore, unlike metals, these devices do not corrode and the modulus of the material may be more closely matched to that of bone. Two polymers that have been used to form bioerodible surgical plates are polylactic acid (PLA) and copolymers of lactic and glycolic acids (PLGA).

The mechanism for bioeroding polymers of lactic acid and copolymers of lactic and glycolic acids is not completely understood. The polymers are probably hydrolyzed in situ to their respective monomers and the resulting monomers are excreted from the body in the urine or expired from the body as carbon dioxide without ill effect. The body's tolerance of these monomers probably results from the fact that lactic acid and glycolic acid are present as natural substances within tissue.

Although polymers of, e.g., PLA degrade as desired, plates constructed of PLA have a tendency to "bow" in bone applications and thereby fail to appropriately immobilize fractures with respect to bending movements. This bowing apparently occurs because the side of the plate immediately adjacent the bone is exposed to a different aqueous environment than the side of the plate adjacent soft tissue. As water is adsorbed into the polymer, the polymer swells. Thus the difference in the aqueous environment of the two surfaces of the plate causes a differential in the amount of water entering the plate through each surface. This differential water adsorption results in turn in the differential swelling of the two sides of the plate, with bowing therefore occurring. Thus it is desirable to form a surgical plate from a bioerodible polymer which is dimensionally and geometrically stable.

A related matter of interest in bone repair involves ensuring that the fractured bone ends are properly stabilized when set, and maintaining this stabilization during healing. A bioerodible bone cement could be used to bridge the area of excised bone fragments and thus aid in healing. Secondly, a bioerodible bone cement could additionally be used in conjunction with bone repair proteins (BRPs) to actively promote bone growth, i.e., the bone cement functions as an osteoinductive material. Also, because the rate of infection following total joint replacement surgery may be as high as 11%, it would also desirable to incorporate various antibiotics into the bone cement for slow release at the surgical site to minimize infection. Ideally, therefore, such a bone cement or "grout" should be moldable in the surgical setting, set to form a strong solid, stabilize at the implant site, and support and aid the bone healing process.

With the use of minimally invasive techniques, a bioresorbable and/or osteoconductive bone cement could be used by injecting the cement into the fracture site under fluoroscopic control. This technique would help prevent complications such as repeated displacement, instability and malunion. The use of the cement may also warrant conservative treatment in patients with relative indications for operative management. These patients include older patients in whom long leg casting will be difficult to be mobile in, irreducible fractures, or one which has slipped in a cast, obese legs which limit the capability of casts to maintain reduction, and chronic alcohol abusers. In addition, patients with relative contraindications to operative treatment, such as vascular insufficiency, diabetes mellitus, soft tissue blisters, abrasions, contusions or burns, could be successfully managed in a conservative fashion thus eliminating peri- and postoperative risk factors. Finally, patients with severe osteoporosis may benefit from the use of this osteoconductive bone cement as an adjunct to conservative treatment. Aside from its use in the treatment of ankle and foot fractures, a bioresorbable and osteoconductive cement may be applicable for the treatment of undisplaced or minimally displaced lateral tibial plateau fractures that would normally warrant conservative treatment (depression <1 cm and valgus instability <10 degrees).

Other potential applications include use in spinal fusions, where autologous bone grafting is often necessary and allogeneic bone is used when autologous bone stocks are insufficient. In these cases, an osteoinductive bioresorbable bone cement could serve as a bone substitute.

Thus a need exists for polymeric bioerodible materials which may be used in making bone cements which desirably have a wide range of precure viscosities (to allow injection of the cement to a bone site) and which also desirably incorporate biologically active agents. Such bioerodible bone cements containing biologically active agents for release must be able to protect the agents from damage during curing, and provide buffering capacity to obviate possible inflammatory foreign body response generated by bioerosion of the cement. Lastly, such polymeric bioerodible materials may also be used to make IFDs having dimensional stability during the critical bone setting and healing period.

SUMMARY OF THE INVENTION

The disclosure relates to bioerodible polymeric semi-interpenetrating network ("semi-IPN") alloys which comprise a first bioerodible polymer capable of producing acidic products upon hydrolytic degradation; a second bioerodible polymer, which, preferably via crosslinking, provides a biopolymeric scaffolding or internal reinforcement; and optionally a buffering compound that buffers the acidic products within a desired pH range. In a preferred embodiment, the second bioerodible polymer comprises polypropylene fumarate (PPF) which is cross-linked, desirably by a vinyl monomer such as vinyl pyrrolidone (VP) to form the biopolymeric scaffolding which provides the semi-IPN with the requisite dimensional and geometric stability. A beneficial end use of this material is in the form of internal fixation devices (IFDs) such as bone supports, plates, and pins, and/or bone cements for bone repair which are formed from the semi-IPN alloy disclosed herein.

Another aspect of the invention comprises a bone cement containing a bioerodible polymeric semi-IPN alloy comprising a first bioerodible polymer (such as PLGA) capable of producing acidic products upon hydrolytic degradation; and a second bioerodible polymer (such as PPF), which provides a biopolymeric scaffolding or internal reinforcement, wherein the second bioerodible polymer is polymerized in vivo to provide a hardened, semi-IPN alloy bone cement. Both the bone cement and dimensionally and geometrically stable IFDs of the disclosure of the invention may advantageously also contain other agents such as bone repair proteins (BRPs) and antibiotics, to, e.g., actively promote bone growth and prevent infection while the bone cement or IFD is in place.

BRIEF DESCRIPTION OF THE DRAWINGS

The invention will be more fully understood by reference to the following Detailed Description Of The Invention in conjunction with the following Drawings, of which.

DETAILED DESCRIPTION OF THE INVENTION

Figure 1A:
FIGS. 1a and 1b are scanning electron micrographs (at 6250×) of a bone cement alloy according to the disclosure containing crosslinked PPF scaffolding and PLGA/calcium gluconate after one and two weeks exposure to water.

The bioerodible bone cements and internal fixation devices (IFD) made from the bioerodible polymeric semi-IPN alloy material disclosed herein may be advantageously used for surgical repair of orthopaedic and maxillofacial fractures. The bioerodible material is a polymeric semi-IPN alloy which comprises at least a first bioerodible polymer capable of producing acidic products upon hydrolytic degradation; and a second bioerodible polymer, which upon crosslinking provides a biopolymeric scaffolding or internal reinforcement.

An semi-interpenetrating polymer network (semi-IPN) is defined herein as an internecine combination of two or more polymers, at least one of which is crosslinked (sometimes in the immediate presence of the other) to form a network ("scaffolding" in the present disclosure) in which the other polymer is enclosed, trapped or retained.

As used herein, the term "bioerodible" is defined as the susceptibility of a biomaterial to degradation over time, usually months. "Buffer" is defined as any material which limits changes in the pH in the implant or cement and its near environment only slightly upon exposure to acid or base. "Acidic product" is defined herein as any product that has a pH less than 7.

The semi-IPN alloy of the invention includes a first bioerodible polymer that undergoes hydrolysis to produce acidic products when exposed to an aqueous medium. Examples of such bioerodible polymers include poly (lactide-co-glycolide) (H[—OCHR—CO—]$_n$OH, where R is H or CH$_3$) ("PLGA"); polydioxanone, poly($\epsilon$-caprolactone); polyanhydrides; poly(ortho esters); copoly (ether-esters); polyamides; polylactones; polypropylene fumarates (H[—O—CH(CH$_3$)—CH$_2$—O—CO—CH=CH—CO—]$_n$OH); and combinations thereof. In a preferred embodiment, the polymer poly(lactide-co-glycolide) H[—OCHR—CO]$_n$OH, R=H, CH$_3$ (PLGA) is used. The PLGA polymers used according to the invention have a lactide to glycolide ratio in the range of 0:100% to 100:0%, inclusive, i.e., the PLGA polymer can consist of 100% lactide, 100% glycolide, or any combination of lactide and glycolide residues. These polymers have the property of degrading hydrolytically to form lactic and glycolic acids.

Selection of a suitable first bioerodible polymer is based primarily on the known properties of the polymer such as polymer strength, rate of hydrolytic degradation, etc. One of ordinary skill in the art may take these and/or other properties into account in selecting a particular polymer for a particular application. Thus, such a selection of a particular polymer is within the skills of the ordinary skilled practitioner.

The second bioerodible polymer of the disclosed semi-IPN alloy may be of a type that undergoes hydrolysis to produce acidic products when exposed to an aqueous medium, such as polydioxanone, poly($\epsilon$-caprolactone); polyanhydrides; poly(ortho esters); copoly(ether-esters); polyamides; polylactones; polypropylene fumarates; and combinations thereof. However, the second bioerodible polymer, preferably upon crosslinking, additionally provides the biopolymeric scaffolding or internal reinforcement which gives the bioerodible polymeric semi-IPN alloy its superior mechanical properties. (As such, the second polymer is desirably different from the first.) This scaffolding is desirably obtained by crosslinking the second bioerodible polymer. Crosslinking may take place, e.g., in a bone cement shortly before or after the cement ingredients have been introduced to the bone fissure or junction. When making an alloy material for IFDs crosslinking may be effected: a) with the first and second bioerodible polymers in cosolution via chemical crosslinking or by irradiation (e.g., γ-irradiation); b) by melt mixing the first and second bioerodible polymers, then irradiating to crosslink the second bioerodible polymer; or c) by forming the biopolymeric scaffolding first via chemical crosslinking or by irradiation, then impregnating the scaffolding with the first bioerodible polymer.

In an advantageous embodiment the second bioerodible polymer comprises polypropylene fumarate, which may be desirably crosslinked using vinyl monomers such as vinyl pyrrolidone (VP). An advantage of VP crosslinking of PPF is that the crosslinks terminate at hydrolytically labile fumarate ester bonds, making the crosslinked network hydrolytically degradable. Furthermore, the hydrolysis products are highly soluble and hence the scaffolding (and thus the entire alloy) is truly resorbable. The crosslinking reaction should preferably seek to minimize homopolymer formation. Other crosslinking monomers such as methyl methacrylate (MMA) may also be used as long as bioerodibility is not compromised. A high PPF:VP ratio favors crosslinking; because the crosslinking reaction is carried out in solution, low concentrations of VP may be used. The degree of crosslinking necessary to form the scaffolding will depend on the particular application, i.e., the relative hardness or rigidity desired, but generally crosslinking of about 5% to 50% of the available crosslinking sites is acceptable, more particularly 5% to 30%.

The bioerodible material of the invention may include a buffering compound which may be a base or base-containing material capable of reacting with the acidic products generated upon hydrolysis of the bioerodible polymer. Since the bioerodible polymers undergo hydrolysis in the body and generate acidic products that cause irritation, inflammation, and swelling (sterile abscess formation) in the treated area, the inclusion of buffer in the bioerodible material counteracts this effect by neutralizing the acidic degradation products and thereby reducing the sterile abscess reaction. The buffer included in the bioerodible material of the invention maintains the pH surrounding the area of surgery to approximately neutrality (i.e., pH 7), or any other pH chosen by the surgeon. Preferably, the pH is maintained in the range of 6–8, and more preferably in the range of 6.8–7.4.

Exemplary buffering materials include inorganic acid salts, organic acid salts, or polymeric organic acid salts. Preferably, the calcium salts of weak acids are used, such as calcium carbonate, although calcium phosphate, calcium acetate, calcium citrate, calcium succinate, and calcium gluconate may also be used. Polymeric buffers may also be used as buffering compounds according to the invention. Suitable polymeric buffers preferably include basic groups which neutralize the acidic products generated upon hydrolysis of the bioerodible polymer. Such polymeric buffers include hydrolytically stable polymers, such as polyamines, poly(N-vinyl carbazole), poly(N-vinyl pyrrolidone), poly(acrylic acid), poly(acrylamide), or a copolymer based on acrylic acid. Another class of buffering compounds useful in the materials and methods of the invention are compounds which, on exposure to water, hydrolyze to form a base as one reaction product. The generated base is free to neutralize the acidic products produced upon hydrolysis of the bioerodible polymer. Compounds of this type include aryl or alkyl carbamic acids and imines. The base-generating compounds used according to the invention offer the advantage that the rate of hydrolysis of the base generator may be selected to correlate to the rate of hydrolysis of the bioerodible polymer.

The inclusion of soluble buffering materials such as those disclosed herein (such as a combination of citric acid and sodium bicarbonate; calcium acetate, and calcium gluconate) also have an important second function in vivo. Upon exposure to aqueous media such as tissue fluids these compounds dissolve almost immediately, leaving pores in the material, whether it be a cement or IFD. (In the case of the citric acid and sodium bicarbonate combination, upon exposure to water in vivo form $CO_2$ and water, leaving holes in place of the solid chemical.) These pores facilitate bone cell migration into the device or cement, and thus serve as osteoconductive pathways for bone healing. Pore size may be controlled by controlling the size of the soluble material introduced to the alloy, i.e., by grinding and sieving the filler to select the appropriate particle size range.

Figure 1B:
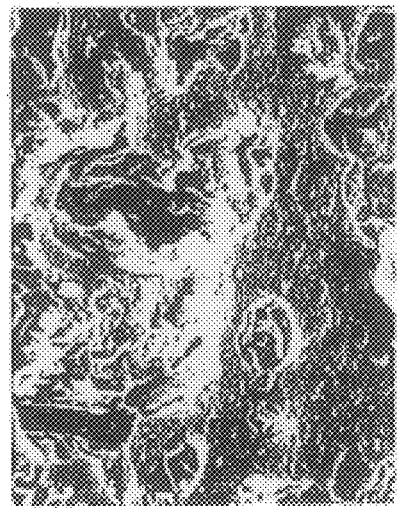

The development of such pores is illustrated in FIGS. 1A and 1B, which are SEM (Amray AMR-1000 SEM at 6250×) of a bone cement alloy containing crosslinked PPF scaffolding and PLGA/calcium gluconate after one and two weeks exposure to water. The alloy was subjected to conditions similar to placement in vivo, over a period of weeks. The development of pores in the alloy, where none were detectable at the start of the experiment, is seen. The holes measure about 3–6 microns on average, but larger holes of 10–15 microns were also seen.

It has been surprisingly found that a combination of a calcium carbonate and hydroxyapatite has been found to support osteoconductivity and osteoinductivity, i.e., providing a pathway for bone cells to penetrate, as well as inducing movement of bone cells into those pathways, as a way of promoting bony ingrowth as resorption of the alloy progresses.

Other fillers may be included in the alloy (preferably protected by the first bioerodible polymer, as disclosed herein) as alternatives to fillers like calcium carbonate and hydroxyapatite, such as ground, demineralized bone and/or unprocessed cadaver allogenic bone.

The buffering compound preferably has an acid dissociation constant ($K_a$) that is smaller than the acid dissociation constant of the acidic products generated upon hydrolysis of the bioerodible polymer. Alternatively, the buffering compound preferably has a hydrolysis constant that is greater than the hydrolysis constant of the acidic products. Further, the buffering compound preferably is only partially soluble in an aqueous medium. In general, buffers of lower solubility are preferred because buffer loss from the polymer by diffusion will be minimized. Details of determining appropriate buffers, methods and amounts of addition, etc., are disclosed in further detail in pending U.S. patent application Ser. No. 08/626,521, the disclosure of which is incorporated herein by reference.

The semi-IPN alloy of the invention has mechanical properties comparable to human bone, as set forth in Table 1.

TABLE 1

| Stiffness, | | GPa | 1–30 |
|---|---|---|---|
| Bending: | Modulus Strength, | GPa | 6–30[1] |
| | | MPa | 160 |
| Torsion: | Modulus Strength, | GPa | 3.2 (femur) |
| | | MPa | 54.1 (femur) |
| Tension: | Modulus Strength, | GPa | 14.9–18.9 |
| | | MPa | 124–174 |
| Compression: | Modulus Strength, | GPa | 8–9[2] |
| | | MPa | 170 (femur) |

[1] Poly(L-lactide) and Poly(D,L-lactide) reinforced with calcium phosphate fibers
[2] Equine long bones Methods of making a bioerodible material for implantation into a surgical site are further contemplated by the inventors. In one embodiment, the first and second bioerodible polymers (and optional components such as biologically active agents for release into surrounding bone tissue and buffering compounds) are dissolved in solvent and mixed to homogeneity, after which the second bioerodible polymer is treated to create the biopolymeric scaffolding, e.g., by crosslinking. The resulting mixture is cast into a desired form, e.g., a sheet, film, plate, screw, etc., and the solvent is evaporated to produce a (buffered) bioerodible implantable material in film form. The product may be further processed, for example, compacted under pressure, extruded through a die, injection molded, or shaped into a form useful for bone repair. Techniques such as compression molding may be used to form end-use configurations such as screws, plates, etc.; or stock from which IFDs may be machined. A constant pressure hydraulic press such as the Compac Model MPC-40 may be used for molding.

In another embodiment the alloy may be prepared similar to methods disclosed in U.S. Pat. No. 5,456,917 to Wise et al., the text of which is incorporated by reference herein, wherein a bioerodible polymer foam scaffolding is prepared by lyophilization of solutions of the polymer in a suitable solvent, such as glacial acetic acid or benzene. A solution containing the first bioerodible polymer and other ingredients such as active agents, buffers, etc. are then forced into the void volume of the scaffolding by cycles of evacuation (degassing) and repressurization. Solvents for the first bioerodible polymer and active agent include water and other solvents which do not dissolve the first bioerodible polymer or change its structure or morphology, such as the lower alcohols. The solvent is then removed by a second lyophilization, and the resulting alloy may be further processed.

The invention also relates to bioerodible bone cements for both orthopaedic repair and for controlled release of a biologically active agent in, if necessary, a protecting polymeric envelope. The bone cement and method of making it encompasses a range of cement materials, the properties of which depend upon the concentration of components to enable preparation of cements of initial (precure) low viscosities which can be delivered by injection to its intended site or cements of higher viscosity which may be molded, e.g., as a putty, to fractures or surgical sites of complex topography.

The first bioerodible polymer, as noted above, may be loaded with an active agent to provide a controlled release of the active agent as the alloy is resorbed. Control of the release rate is achieved by incorporating the active agent in a protecting envelope of the first bioerodible polymer. In addition, further control of the release rate is achieved by incorporating non reactive fillers of varying solubility (such as hydroxyapatite) into the alloy. Any type of active agent may be incorporated into the first bioerodible polymer, including without limitation drugs, hormones, antibiotics, cells etc.

The bone cement of the invention comprises the first and second bioerodible polymers as set forth herein. Other desirable components of the cement include biologically active or therapeutic agent(s), cross linking agent (such as a vinyl monomer); an initiator for the cross linking reaction between the second bioerodible polymer and the crosslinking agent; and accelerator(s) and inhibitor(s) to control the cure kinetics. Further components of the material of the invention include biologically inert solid fillers, liquid (aqueous or non-aqueous) diluents for viscosity control and for solubilization of components, and wetting agents (surface active agents or detergents) to facilitate mixing of components and contact of the mixed components with tissue.

The cement may be advantageously prepared as a two or three part formulation, in which the initiator and accelerator, or initiator and components for forming the scaffolding, e.g., second bioerodible polymer and crosslinker, are kept separate until the parts are combined. The combined parts are allowed to cure in situ (at the surgical or fracture site) to aid in maintaining fracture reduction or to fill defects or other openings in bone following surgery. Keeping the system parts separate prior to use ensures against premature reaction, to increase pre-use stability and shelf life.

In a preferred embodiment the second bioerodible polymer is PPF, which is crosslinked polymerization between PPF and a vinyl monomer such as vinyl pyrrolidone or methyl methacrylate. The vinyl polymerization employs an initiator such as benzoyl peroxide; other initiators may be used. Accelerators such as N,N-dimethyl-p-toluidine (DMPT) and inhibitors such as hydroquinone (HQ) or t-butylhydroquinone (TBHQ) may also be included to control cure reaction kinetics. Other components such as detergents and water may be included as processing aids to adjust viscosity and to improve workability of the cement.

The composition of the cement may be varied according to requirements of cure time, viscosity, loading of biologically active or therapeutic agent(s), and degradation rates. Component ranges (range 2=particularly preferred range) are given in Table 2.

TABLE 2

| Component | Range 1 (% wt) | Range 2 (wt %) |
|---|---|---|
| First bioerodible polymer | 0–50 | 3–15 |
| Second bioerodible polymer | 5–60 | 30–50 |
| Cross linking agent | 5–50 | 8–12 |
| Therapeutically inert liquid diluent | 0–50 | 10–20 |
| Active agent protected by first bioerodible polymer | 1–50 | |
| Initiator | 0–5 | 0.5–1.5 |
| Inhibitor | 0–5 | |
| Accelerator | 0–5 | |
| Water | 0–1 | |
| Detergent | 0–1 | |
| Soluble buffering material | — | 3–12 |
| Less soluble buffering material/osteoinductive agent | — | 5–20 |

One embodiment of a two part system is comprised as follows:

| Part A | Part B |
|---|---|
| PPF | Inert Fillers |
| Vinyl Monomer | PLGA/biologically active or therapeutic agent(s) |
| Accelerator | Initiator |
| Diluents | Inhibitor |

This two part formulation 1) separates the polymerizable components from the initiator; and 2) separates the protected biologically active or therapeutic agent(s) from the liquid components, which prevents premature release of the biologically active or therapeutic agent(s) from the first bioerodible polymer.

A typical embodiment of a three part system is shown below.

| Part A | Part B | Part C |
|---|---|---|
| PPF | Initiator | Inert Fillers |
| Vinyl Monomer | Diluents | Accelerator |
| Inhibitor | | PLGA/biologically active or therapeutic agent(s) |

An advantage of the three part formulation is that it separates the biologically active or therapeutic agent(s) from the initiator, which is the least thermally stable component of the cement.

Incorporation of biologically active or therapeutic agent(s) into the first bioerodible polymer provides several advantages for the controlled release feature of the invention. The first bioerodible polymer, such as PLGA, functions as a protective coating to prevent the biologically active or therapeutic agent(s) from reacting with the components of the cement. Thus it is possible to maintain the full potency of the biologically active or therapeutic agent(s) during the cure process. In addition, possible reactions of the biologically active or therapeutic agent(s) with the free radicals generated during the curing process is minimized because the time during which the cement changes from a fluid or viscous putty to a hard mass is short (about ten minutes). The first bioerodible polymer also functions to moderate the release of the biologically active or therapeutic agent(s).

EXAMPLE 1

Several experiments were conducted to demonstrate PPF crosslinking with vinyl pyrrolidone (VP) in glacial acetic acid (gl HAc) solution in the presence of PLGA-85:15. gl HAc is a suitable solvent for several reasons: 1) traces remaining in the product will not be toxic; 2) its vapor pressure at its freezing point is high (FP=16.7° C.; VP at 17.5° C.=10 mm Hg). This property allows formation of alloys of the disclosure by lyophilization to remove the solvent.

The following samples were prepared as shown in Table 3.

TABLE 3

| — | 39–1 | 39–2 | 40–1 | 40–2 | 40–3 | 41–1 |
|---|---|---|---|---|---|---|
| PLGA, g | — | — | — | — | — | 0.350 |
| PPF, g | 0.979 | 0.999 | 0.979 | 0.998 | 0.956 | 0.954 |
| VP, g | 2.267 | 2.000 | 2.165 | 2.165 | 2.190 | 2.167 |
| B P, g(1) | 0.134 | 1.381 | 0.136 | 0.139 | 0.134 | 0.139 |
| gl HAc, ml | 10 | 10 | 10 | 10 | 10 | 10 |
| R x T° C.(2) | 90 | 90 | RT | 70 | 60 | 70 |
| R x t min(2) | 25 | 10 | 6 mos | 31 | 100 | 30–40 |

(1)BP = benzoyl peroxide
(2)Rx T° C.; Rx t min = reaction temperature and time

Prior to heating, all samples were completely dissolved in gl HAc. After heating at the temperature and for the time indicated, a continuous solid phase had formed in all samples. Solubility tests on these samples indicated that crosslinking preferentially occurred over PVP homopolymer formation. Lyophilization of PPF/VP/BP and PLGA/PPF/VP/BP crosslinked in gl HAc results in porous solids.

The following describes an exemplary procedure for preparing a bioerodible semi-IPN alloy in accordance with the invention.

(a) Removal of NaOH Inhibitor from VP. VP (1-vinyl-2-pyrrolidone, Aldrich lot 07401BQ) contained 1% inhibitor of NaOH. Separation of NaOH from the VP was accomplished by a vacuum distillation of the VP/NaOH solution. The distilled VP was collected by condensing VP vapor with cold water, while the NaOH was left in the distillation flask.

(b) Crosslinking of PPF (X-PPF) with VP in Glacial Acetic Acid. At room temperature, 1.0 g PPF [CSI, lot 48-86-2, Mw. 7277] and 1.1 g DVP were co-dissolved in 10 ml gl HAc (Fisher lot 905039) in a lyophilization flask. 0.13 g of a preground BP powder (Aldrich lot 06428CW) was then added to the solution in the flask. After the BP dissolved completely, the solution showed a clear amber color. The lyophilization flask was placed in a preheated silicon oil bath with a temperature of 773° C. After 15 minutes in the bath, the solution started turning white and cloudy, indicating crosslinking. After another 5 minutes in the bath, the solution became a pale yellow "jelly." The flask was then removed from the bath to a freezer with a temperature of −10° C. The flask was stored in the freezer for over 12 hours before it was lyophilized.

(c) Lyophilization of X-PPF/GlHAc Solution. The lyophilization flask, now containing the frozen X-PPF/GlHAc solution, was placed in an ice bath and was connected to a lyophilization setup which consisted of a solvent trap and a reduced pressure at 1 mm Hg. The lyophilization proceeded until all the GlHAc was collected in the trap.

(d) Removal of Unreacted VP and PVP. The removal of unreacted compounds was accomplished by impregnating the foam with water by successive cycles of evacuation and admission of air. The washed foam was dried in an oven with a temperature set at 50° C.

(e) Impregnation of X-PPF Foam Scaffolding with PLGA: PLGA-85:15 (PLGA-85:15, B.I. lot 25024, Mw 11500.) was introduced by immersing the foam in a solution of PLGA in GlHAc, evacuating to remove air from the foam and repressurizing to force the PLGA solution into the foam scaffolding. A second lyophilization was used to remove the GlHAc, leaving the PLGA in the scaffolding. The ratio of PLGA deposited to the foam was 52.4 w/w %.

The product was desirably washed with water to extract any PVP that has been formed. IFDs may be formed from the material as disclosed herein.

EXAMPLE 2

High viscosity cements or putties according to the disclosure using VP crosslinker were prepared as a two part formulation of variable composition, as shown in Table 4, which presents the weights of the components and the weight fractions of the PPF, calcium phosphate and VP.

TABLE 4

Composition of Cement Formulations

| Sample | Composition (g) | | | | | Weight Fraction | | |
|---|---|---|---|---|---|---|---|---|
| | PPF* | CP | VP | BP | DMPT/VP† | f(PPF) | f(CP) | f(VP) |
| 45-75-1 | 1.0012 | 0.0000 | 1.0006 | 0.0604 | 0.0000 | 0.4855 | 0.0000 | 0.4852 |
| 45-75-2 | 1.0000 | 0.0000 | 0.6004 | 0.0604 | 0.0000 | 0.6022 | 0.0000 | 0.3616 |
| 45-75-3 | 1.0000 | 0.0000 | 1.0070 | 0.0000 | 0.0026 | 0.4831 | 0.0000 | 0.4877 |
| 45-87-2A | 1.0000 | 1.0007 | 1.0012 | 0.0605 | 0.0028 | 0.3262 | 0.3265 | 0.3275 |
| 45-87-2B | 1.0007 | 0.9997 | 1.0009 | 0.0607 | | | 0.3261 | 0.3276 |
| 45-110-1 | 1.0003 | 1.0001 | 0.5029 | 0.0605 | | | 0.3893 | 0.1978 |
| 45-110-2 | 1.0000 | 1.0004 | 2.0024 | 0.0606 | | | 0.2460 | 0.4932 |
| 45-110-3 | 1.0000 | 1.0001 | 2.9996 | 0.0603 | | | 0.1974 | 0.5933 |
| 45-132-1 | 1.0005 | 1.0000 | 1.5049 | 0.0605 | | | 0.2801 | 0.4227 |
| 45-132-2 | 1.0000 | 1.0001 | 2.4998 | 0.0600 | | | 0.2190 | 0.5489 |
| 45-123-3 | 1.0000 | 1.0007 | 3.0005 | 0.0605 | | | 0.1976 | 0.5930 |

*PPF sample 48-86-2, $M_\phi = 6651$; $M_n = 2587$, polydispersity
†Concentration of DMPT in VP = 0.48% (w/w)

Components of Parts A and B are summarized below:

| Part A: | PPF (Wt. Avg. Mol. Wt. = 6650, polydispersity = 2.57) |
| | Tribasic calcium phosphate (hydroxyapatite) (approximately $Ca_{10}(OH)_2(PO_4)_6$) |
| | Vinyl pyrrolidone (cross linking vinyl monomer) |
| | N,N-Dimethyl-p-toluidine (accelerator) |
| Part B: | Vinyl Pyrrolidone |
| | Benzoyl peroxide (initiator) |
| | hydroquinone (inhibitor) |

Figure 2:
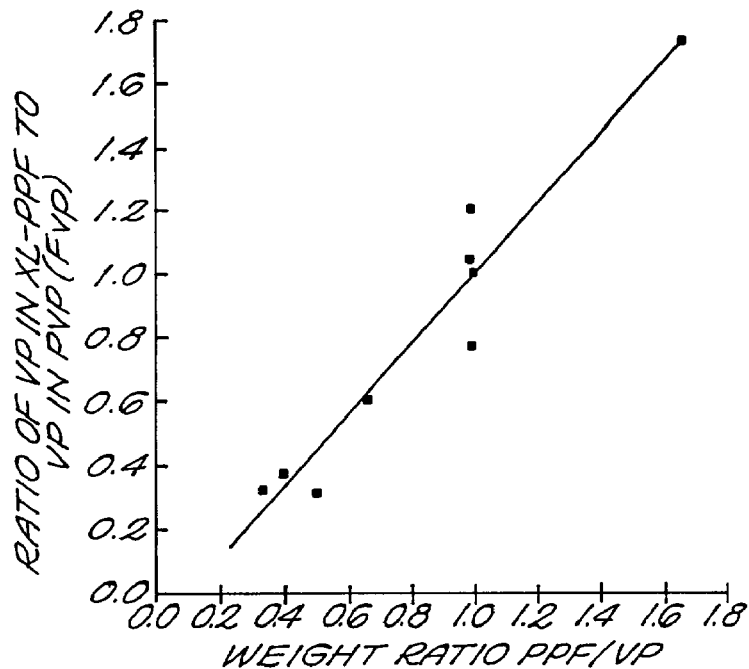
FIG. 2 is a graph of distribution of vinyl pyrrolidone between crosslinked poly(propylene fumarate) and poly (vinyl pyrolidone). Linear regression analysis: intercept=−0.082; slope=1.084; correlation coefficient=0.9686. (Example 2.)
Figure 3:
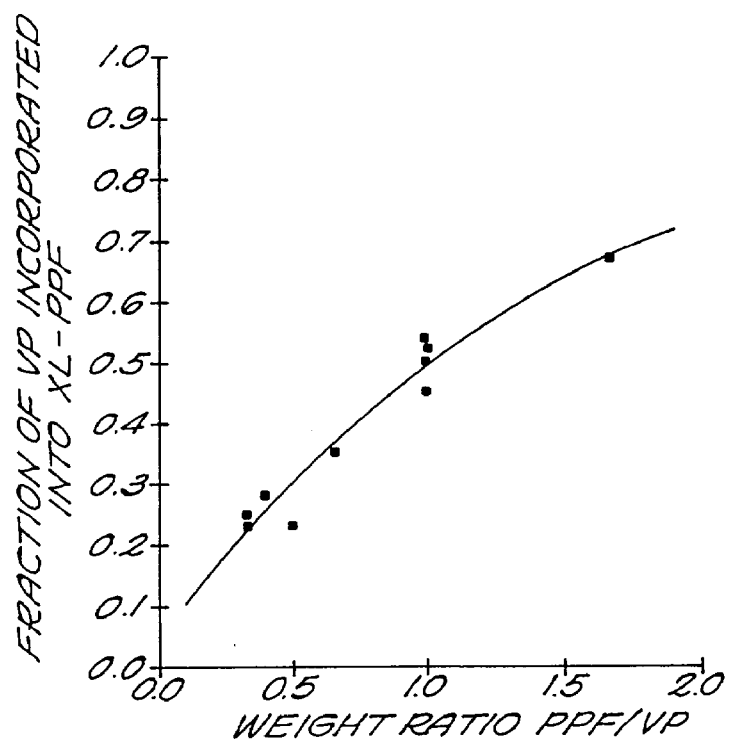
FIG. 3 is a graph of weight fraction of vinyl pyrrolidone incorporated into crosslinked poly(propylene fumarate) as a function of PPF/VP weight ratio. (Example 2.)

Samples were cured in sealed vials. After curing the samples were ground, weighed, washed with water to extract soluble components, and dried to constant weight. The remaining insoluble material was then extracted with tetrahydrofuran to remove uncrosslinked PPF. In all cases almost all of the PPF was crosslinked: >98% in 6 out of 9 samples, and >86% in the remaining three samples. Further, the percent of PPF crosslinked was independent of composition, i.e., independent of filler, accelerator, initiator, or monomer. On the other hand, the fraction of VP which was incorporated into the scaffolding depended strongly on the ratio of PPF/VP, increasing with increasing PPF/VP ratio. The ratio of VP incorporated into the crosslinks varied linearly with the PPF/VP ratio. These results are summarized in Table 5 and presented graphically in FIGS. 2 and 3. The significance of these results can be appreciated if we define two quantities. The density of crosslinks between PPF chains can be defined as dcl=(moles of crosslinks/mole of PPF) and the average length of crosslinks can be defined as lcl=(moles of VP/mole of PPF). Thus (dcl)(lcl)=(mole of VP/mole of PPF). Thus by varying the PPF/monomer ratio, control of the product (dcl)(lcl) can be exercised.

TABLE 5

Fraction of VP and PPF Incorporated into Crosslinked PPF and Distribution of VP between XL-PPF and PVP

| Sample | PPF/VP | Ff⇒ | Fρ† | F. Mean ± SD‡ | Fppf§ | Fρρ| |
|---|---|---|---|---|---|---|
| 45-75-1 | 1.0006 | 0.5554 | 0.5007 | 0.5281 ± 0.0387 | 0.9941 | 1.0038 |
| -2 | 1.6656 | 0.7097 | 0.6332 | 0.6715 ± 0.0541 | 0.9858 | 1.7260 |
| -2 | 0.9905 | 0.5725 | 0.5127 | 0.5426 ± 0.0423 | | 1.0519 |
| -87-2A | 0.9960 | 0.4649 | 0.5463 | 0.5056 ± 0.0576 | 0.8571 | 1.2042 |
| 87-2B | 0.9966 | 0.4727 | 0.4349 | 0.4538 ± 0.0267 | 0.9773 | 0.7695 |
| -110-1 | 1.9693 | | 0.4970 | 0.4970 | | |
| -2 | 0.4985 | 0.2206 | 0.2472 | 0.2314 ± 0.0153 | 0.9937 | 0.3196 |
| -3 | 0.3326 | 0.2222 | 0.2449 | 0.2336 ± 0.0161 | 0.8714 | 0.3243 |
| -132-1 | 0.56630 | 0.3272 | 0.3764 | 0.3518 ± 0.0348 | 0.8656 | 0.6035 |
| -2 | 0.3989 | 0.2893 | 0.2747 | 0.2820 ± 0.0103 | 0.9812 | 0.3787 |
| -3 | 0.3330 | 0.2238 | 0.2634 | 0.2486 ± 0.0209 | 0.9953 | 0.3297 |

⇒Fraction of VP in XL-PPF calculated by material balance based on PPF.
†Frace of VP in XL-PPF calculated by material balance based on VP.
‡F = mean ± standard deviation of F ⌈ and Fρ (mean Fρρf = 0.9469 ± 0.0619).
§Fraction of PPF which is crosslinked.
|Distribution of VP between XL-PPF and PVP.

Varying the PPF/monomer ratio will also vary the viscosity of the cement if the crosslinking monomer is the only liquid component. However, the viscosity may be controlled independently as described by various diluents which may be liquid to reduce viscosity or solid fillers, such as tribasic calcium phosphate (hydroxyapatite), to increase viscosity.

EXAMPLE 3

A low viscosity injectable cement may be formulated using VP both for cross linking PPF, and to control the initial viscosity. The cement can also be reformulated by substituting one of several acceptable solvents for part of the VP. In this example, this change is in Part B, which contains no monomer (VP). Acceptable solvents include propylene glycol, poly(ethylene glycol), and peanut oil. Cure rate and hardness are not compromised by this substitution. The advantages of this substitution are threefold. First, VP is miscible with these solvents as well as with water. By creating a more lipophilic environment the rate at which VP diffuses from the injection site is diminished, thus allowing a greater portion to be incorporated into the scaffolding. Minimizing diffusion into surrounding tissue is expected to diminish inflammatory response. A second advantage is that being more dilute, the probability of crosslinking with PPF is increased and that of homopolymer formation is reduced. A third advantage is increased stability. The initiator, included in Part B is now dissolved in PO rather than in the monomer VP thus eliminating premature polymerization in that part. The formulations are given in Table 6.

In this example peanut oil has been used to replace a portion of the VP, and accounts for 50% by weight of the liquid components. The Shore D hardness of IC's formulated with PO were measured as 45–50. This is comparable to polystyrene, 65; poly(ethylene), 40; and PTFE, 50.

TABLE 6

COMPOSITION OF REFORMULATED INJECTABLE
BONE CEMENT (Weight %)

|  | Part A | Part B |
|---|---|---|
| PPF | 37.1 | PO 25.1 |
| VP | 25.0 | BP 0.6 |
| CaAc2 |  | 12.0 |
| DMPT |  | 0.2 |

PPF = poly(propylene fumarate)
VP = vinyl pyrrolidone (crosslinking agent)
CaAc2 = calcium acetate (soluble filler)
DMPT = dimethyl-p-toluidine (accelerator)
BP = benzoyl peroxide (initiator)
PO = peanut oil (diluent)

The initial (precure) viscosity of the reformulated cement is determined by both the solids to liquid ratio and the viscosities of the fluid components (VP and PO). More important than the actual viscosity value is the force a surgeon must exert on the piston of a syringe containing the cement in order to expel it. To evaluate this flow rates of glycerol, peanut oil, and the injectable cement through a syringe equipped with a 15 gauge (0.137 cm i.d.) by 1.5" (3.81 cm) length were measured. Pressure on the piston was applied with weights of 0.5, 1.0, and 2.0 kg and flow of a given volume was timed. Mean flow rates under a given force are indicated in Table 7.

TABLE 7

MEAN FLOW RATES (cm³/sec)

| Weight on Piston (kg) | Pressure (gram/cm²) | Flow Rates, cm³/sec | | |
|---|---|---|---|---|
| | | Glycerol | Cement | Peanut Oil |
| 0.5 | 283 | 0.001 | 0.001 | — |
| 1.0 | 566 | 0.054 + 0.003 | 0.169 + 0.034 | — |
| 2.0 | 1132 | 0.145 + 0.008 | 0.342 + 0.012 | 2.59 + 0.22 |

The pressure exerted by these weights, calculated by dividing the weight by the cross sectional area of the syringe barrel, are easily achieved by normal thumb pressure. The slow flow rates observed at 0.5 kg is due to the frictional resistance of the piston. Exerting the highest pressure (1132 g/cm²), 5 cc of cement can be delivered in less than 15 seconds.

EXAMPLE 4

The effect of temperature and accelerator on cure time in injectable bone cements in accordance with the invention was studied. The mixture of Example 3 was used with the following changes. VP may be used as an alternative to the crosslinking agent methyl methacrylate (MMA) and propylene glycol may be used as a solvent for PPF or as a diluent. Calcium phosphate tribasic (hydroxyapatite, "HA") is used as an relatively insoluble filler. The initiator is benzoyl peroxide and was used without an accelerator. In this example, reaction at room temperature is slow, but increases when heat is applied. In all cases the formulations are sufficiently liquid for injection. The data are shown in Table 8.

The formulations may also be varied by including an accelerator in either part A or part B, and an initiator in the other part. A soluble filler may also be included. In the examples given in Table 9 no non-reacting solvent is used. Liquid monomer (MMA or VP) but no PG is used in these formulations. The soluble filler calcium acetate (CaAc2) is used in place of HA. Cure proceeds rapidly at room temperature with VP but more slowly when MMA is substituted for VP. The location of the initiator may be in either Part A or Part B as long as the accelerator is in the other part, with no effect on stability (when stored cold) or reaction rates. Table 9 describes these formulations. All pre-cure viscosities are sufficiently low for injection.

TABLE 8

Injectable Cements Using Propylene Glycol as a Non-Reacting Solvent:
No Accelerator

| | Experiment | | | | | |
|---|---|---|---|---|---|---|
| | 1 | 2 | 3 | 4 | 5 | 6 |
| Part A | | | | | | |
| PPF:PG = 1:1*, ml | 1.0 | 1.0 | 1.0 | 1.0 | 1.0 | 0.30 |
| HA, gram | 0.2 | 0.2 | 0.4 | 0.4 | 0.6 | 0.25 |
| Part B | | | | | | |
| VP:BP = 1.0:0.5**, ml | 1.0 | 0.5 | 0.5 | 0.5 | 0.4 | 0.12 |
| Temperature, ° C. | 71 | 71 | 71 | 36 | 71 | 71 |
| Cure Time, min. | 2 | 2 | 1 | 19 (hr) | 2.5 | 2.5 |

*1.0 gram PPF/1.0 ml PG
**1.0 ml VP/0.5 gram BP

TABLE 9

Injectable Cements with Accelerator and Soluble
Filler: No Solvent or Diluent

| Experiment | A | B | 1 | 2 |
|---|---|---|---|---|
| Part A | | | | |
| PPF*, gram | 1.50 | 1.00 | 1.50 | 1.50 |
| VP, gram | 1.00 | — | — | 1.00 |
| MMA, gram | — | 1.78 | 1.00 | — |
| CaAc2, gram | 0.10 | 1.60 | 0.10 | 0.50 |
| BP, gram | — | 0.15 | — | — |
| DMPT, gram | 0.01 | — | 0.01 | 0.01 |

TABLE 9-continued

Injectable Cements with Accelerator and Soluble Filler: No Solvent or Diluent

| Experiment | A | B | 1 | 2 |
|---|---|---|---|---|
| Part B | | | | |
| VP, gram | 0.50 | — | — | 0.50 |
| MMA, gram | — | 0.34 | 0.50 | — |
| BP, gram | 0.025 | — | 0.025 | 0.025 |
| DMPT, gram | — | 0.016 | — | — |
| Cure time, minutes | 0.3–0.5 | >10 | >10 | 0.5 |

Having disclosed the preferred embodiments, those skilled in the art will realize many variations are possible which will still be within the spirit and scope of the claimed invention. Therefore, it is the intention to limit the invention only as indicated by the scope of the claims.

What is claimed is:

1. A two part bioerodible bone cement system which, upon mixing of the system parts, forms a bioerodible polymeric semi-IPN alloy, said two part cement system consisting of
   a) a first part comprising a first bioerodible polymer capable of producing acidic products upon hydrolytic degradation, crosslinking initiator, and a therapeutically effective amount of a biologically active or therapeutic agent, wherein said biologically active or therapeutic agent is in a protective coating of said first bioerodible polymer; and
   b) a second part comprising a second bioerodible scaffolding polymer, which upon crosslinking provides a biopolymeric scaffolding or internal reinforcement for said semi-IPN alloy, and crosslinking agent for said second bioerodible scaffolding polymer.

2. The bone cement system of claim 1 further comprising in one of said parts a buffering compound in sufficiently high concentration so as to buffer said acidic products within a desired pH range.

3. The bone cement system of claim 1 wherein said second bioerodible polymer comprises polypropylene fumarate (PPF).

4. The bone cement system of claim 3 wherein said crosslinking agent is a vinyl monomer.

5. The bone cement system of claim 4 herein said crosslinking agent is vinyl pyrrolidone.

6. The bone cement system of claim 3 wherein said crosslinking agent is methyl methacrylate (MMA).

7. The bone cement system of claim 1 wherein said biologically active or therapeutic agent is selected from the group consisting of bone repair proteins, antibiotics, cells, and mixtures thereof.

8. The bone cement system of claim 1 wherein said first bioerodible polymer is different from said second bioerodible polymer.

9. The bone cement system of claim 1 wherein said first bioerodible polymer is selected from the group consisting of poly(lactide-co-glycolide) (PLGA); polydioxanone; poly(ε-caprolactone); polyanhydrides; poly(ortho esters); copoly(ether-esters); polyamides; polylactones; polypropylene fumarates $(H(-O-CH(CH_3)-CH_2-O-CO-CH=CH-CO-)_nOH)$; and combinations thereof.

10. The bone cement system of claim 2 wherein said buffering compound that buffers said acidic products within a desired pH range is selected from the group consisting of inorganic acid salts; organic acid salts; and polymeric organic acid salts.

11. The bone cement system of claim 2 wherein said buffering compound is selected from the group consisting of calcium carbonate, calcium phosphate, calcium acetate, calcium citrate, calcium succinate, hydrolyzable polyamines, poly(N-vinyl carbazole), poly(acrylic acid), poly(acrylamide), and mixtures thereof.

12. The bone cement system of claim 2 wherein said buffering compound is selected from the group consisting of calcium carbonate, calcium phosphate, calcium acetate, calcium citrate, calcium succinate, and mixtures thereof; said alloy further comprising an osteoconductive composition.

13. The bone cement system of claim 2 wherein the particle size of said buffering compound is from about $5\mu$ to $500\mu$.

14. The bone cement system of claim 12 wherein said osteoconductive composition comprises hydroxyapatite.

15. A three part bioerodible bone cement system which, upon mixing of the system parts, forms a bioerodible polymeric semi-IPN alloy, said three part cement system consisting of
   a) a first part comprising a first bioerodible polymer capable of producing acidic products upon hydrolytic degradation and a therapeutically effective amount of a biologically active or therapeutic agent, wherein said biologically active or therapeutic agent is in a protective coating of said first bioerodible polymer;
   b) a second part comprising a second bioerodible scaffolding polymer, which upon crosslinking provides a biopolymeric scaffolding or internal reinforcement for said semi-IPN alloy, and crosslinking agent for said second bioerodible scaffolding polymer; and
   c) a third part comprising crosslinking initiator.

16. The bone cement system of claim 15 further comprising in one of said parts a buffering compound in sufficiently high concentration so as to buffer said acidic products within a desired pH range.

17. The bone cement system of claim 15 wherein said second bioerodible polymer comprises polypropylene fumarate (PPF).

18. The bone cement system of claim 15 wherein said slinking agent is a vinyl monomer.

19. The bone cement system of claim 18 wherein said crosslinking agent is vinyl pyrrolidone.

20. The bone cement system of claim 18 wherein said crosslinking agent is methyl methacrylate (MMA).

21. The bone cement system of claim 15 wherein said biologically active or therapeutic agent is selected from the group consisting of bone repair proteins, antibiotics, cells, and mixtures thereof.

22. The bone cement system of claim 15 wherein said first bioerodible polymer is different from said second bioerodible polymer.

23. The bone cement system of claim 15 wherein said first bioerodible polymer is selected from the group consisting of poly(lactide-co-glycolide) (PLGA); polydioxanone; poly(ε-caprolactone); polyanhydrides; poly(ortho esters); copoly(ether-esters); polyamides; polylactones; polypropylene fumarates $(H(-O-CH(CH_3)-CH_2-O-CO-CH=CH-CO-)_nOH)$; and combinations thereof.

24. The bone cement system of claim 16 wherein said buffering compound that buffers said acidic products within a desired pH range is selected from the group consisting of inorganic acid salts; organic acid salts; and polymeric organic acid salts.

25. The bone cement system of claim 16 wherein said buffering compound is selected from the group consisting of calcium carbonate, calcium phosphate, calcium acetate, calcium citrate, calcium succinate, hydrolyzable polyamines, poly(N-vinyl carbazole), poly(acrylic acid), poly(acrylamide), and mixtures thereof.

26. The bone cement system of claim 16 wherein said buffering compound is selected from the group consisting of calcium carbonate, calcium phosphate, calcium acetate, calcium citrate, calcium succinate, and mixtures thereof; said alloy further comprising an osteoconductive composition.

27. The bone cement system of claim 16 wherein the particle size of said buffering compound is from about $5\mu$ to $500\mu$.

28. The bone cement system of claim 26 wherein said osteoconductive composition comprises hydroxyapatite.

29. A two part bioerodible bone cement system which, upon mixing of the system parts, forms a bioerodible polymeric semi-IPN alloy, said two part cement system consisting of a) a first part comprising a first bioerodible polymer capable of producing acidic products upon hydrolytic degradation, crosslinking initiator, a therapeutically effective amount of a biologically active or therapeutic agent and a combination of citric acid and sodium bicarbonate; and b) a second part comprising a second bioerodible scaffolding polymer, which upon crosslinking provides a biopolymeric scaffolding or internal reinforcement for said semi-IPN alloy, and crosslinking agent for said second bioerodible scaffolding polymer.

30. A three part bioerodible bone cement system which, upon mixing of the system parts, forms a bioerodible polymeric semi-IPN alloy, said three part cement system consisting of a) a first part comprising a first bioerodible polymer capable of producing acidic products upon hydrolytic degradation, and a combination of citric acid and sodium bicarbonate;

b) a second part comprising a second bioerodible scaffolding polymer, which upon crosslinking provides a biopolymeric scaffolding or internal reinforcement for said semi-IPN alloy, and crosslinking agent for said second bioerodible scaffolding polymer; and c) a third part comprising crosslinking initiator.

* * * * *

UNITED STATES PATENT AND TRADEMARK OFFICE
CERTIFICATE OF CORRECTION

PATENT NO. : 6,071,982
DATED : June 6, 2000
INVENTOR(S) : Donald L. Wise et al.

It is certified that error appears in the above-identified patent and that said Letters Patent is hereby corrected as shown below:

Column 12,
Table 5, 6$^{th}$ column heading, "Fppf$_§$" should read -- F$\rho$pf$_§$ --;
Table 5, column 1, row 3, "-2" should read -- -3 --; and Column 16,
Line 41, "slinking" should read -- crosslinking --.

Signed and Sealed this

Twenty-first Day of May, 2002

Attest:

JAMES E. ROGAN
Attesting Officer     Director of the United States Patent and Trademark Office